(12) United States Patent
Orr et al.

(10) Patent No.: US 8,801,625 B2
(45) Date of Patent: Aug. 12, 2014

(54) SYSTEMS AND METHODS FOR ACCURATELY, SUBSTANTIALLY NONINVASIVELY DETERMINING PULMONARY CAPILLARY BLOOD FLOW OR CARDIAC OUTPUT

(75) Inventors: Joseph A. Orr, Park City, UT (US); Kai Kück, Hamburg (DE)

(73) Assignee: RIC Investments, LLC, Murrysville, PA (US)

( * ) Notice: Subject to any disclaimer, the term of this patent is extended or adjusted under 35 U.S.C. 154(b) by 1756 days.

(21) Appl. No.: 11/347,611

(22) Filed: Feb. 3, 2006

(65) Prior Publication Data

US 2006/0129055 A1    Jun. 15, 2006

Related U.S. Application Data

(63) Continuation of application No. 10/400,717, filed on Mar. 27, 2003, now Pat. No. 7,025,731, which is a continuation of application No. 09/510,702, filed on Feb. 22, 2000, now Pat. No. 6,540,689.

(51) Int. Cl.
*A61B 5/02* (2006.01)
*A61B 5/08* (2006.01)

(52) U.S. Cl.
USPC ............ 600/529; 600/504; 600/532; 600/483

(58) Field of Classification Search
USPC .......................... 600/483, 504, 529, 532, 543
See application file for complete search history.

(56) References Cited

U.S. PATENT DOCUMENTS

| | | |
|---|---|---|
| 4,221,224 A | 9/1980 | Clark |
| 4,463,764 A | 8/1984 | Anderson et al. |
| 5,060,656 A | 10/1991 | Howard |
| 5,069,220 A | 12/1991 | Casparie et al. |
| 5,117,674 A | 6/1992 | Howard |
| 5,178,155 A | 1/1993 | Mault |
| 5,285,782 A | 2/1994 | Prosser |
| 5,285,794 A | 2/1994 | Lynch |
| 5,299,579 A | 4/1994 | Gedeon et al. |
| 5,402,796 A | 4/1995 | Packer et al. |
| 5,632,281 A | 5/1997 | Rayburn |

(Continued)

FOREIGN PATENT DOCUMENTS

| | | |
|---|---|---|
| DE | 2849217 A1 | 5/1980 |
| WO | WO 96/24285 | 8/1996 |
| WO | WO 98/12963 | 4/1998 |

OTHER PUBLICATIONS

H. Blomquist et al., *A Non-Invasive Technique for Measurement of Lung Perfusion*, Intensive Care Medicine 1986; 12:172.

(Continued)

*Primary Examiner* — Michael D'Angelo
*Assistant Examiner* — Christian Jang

(57) ABSTRACT

Methods for noninvasively determining a pulmonary capillary blood flow or a cardiac output of a subject include determining data of the amount of gas exchanged between blood and gas in lungs of the subject, as well as data of an indicator of the content of the gas in blood of the subject. Such a determination may be made during two or more different states of ventilation. A geometric relationship is identified between data points, with any data points outlying the geometric relationship being disregarded. The remaining data points may be used to estimate or calculate a measure of pulmonary capillary blood flow or cardiac output. Systems that include elements that are configured to effect such methods are also disclosed.

15 Claims, 6 Drawing Sheets

(56) References Cited

U.S. PATENT DOCUMENTS

| | | | |
|---|---|---|---|
| 5,836,300 | A | 11/1998 | Mault |
| 5,971,934 | A | 10/1999 | Scherer et al. |
| 6,102,868 | A | 8/2000 | Banner et al. |
| 6,135,107 | A | 10/2000 | Mault |
| 6,200,271 | B1 | 3/2001 | Kuck et al. |
| 6,210,342 | B1 | 4/2001 | Kuck et al. |
| 6,217,524 | B1 | 4/2001 | Orr et al. |
| 6,238,351 | B1 | 5/2001 | Orr et al. |
| 6,306,098 | B1 | 10/2001 | Orr et al. |
| 6,394,962 | B1 | 5/2002 | Gama de Abreau et al. |
| 6,402,697 | B1 | 6/2002 | Calkins et al. |
| 6,540,689 | B1 | 4/2003 | Orr et al. |

OTHER PUBLICATIONS

R.J. Bosman et al, *Non-Invasive Pulimonary Blood Flow Measurement by Means of $CO_2$ Analysis of Expiratory Gases*, Intensive Care Medicine 1991, 17:98-102.

A. Gedeon, *Non-Invasive Pulmonary Blood Flow for Optimal Peep*, ICOR AB, Ulvsundavagen 178 B, S-161 30 Bromma, Sweden, pp. 49-58. (1992).

Capek, J.M., *Noninvasive Measurement of Cardiac Output Using Partial $CO_2$ Rebreathing* [Dissertation], Rensselaer Polytechnic Institute (1988) 28:351 p. (due to large number of pages, only table of contents and abstract have been copied).

Capek, J.M., et al., *Noninvasive Measurement of Cardiac Output Using Partial $CO_2$ Rebreathing*, IEEE Trans. Biomed. Eng. (1988) 35(9):653-61.

Davies, Gerald G., et al., *Continuous Fick cardiac output compared to thermodilution cardiac output*, Critical Care Medicine (1986) 14(10):881-85.

Elliot, C. Gregory, et al., *Complications of Pulmonary Artery Catheterization in the Care of Critically Ill Patients*, Chest (1979) 76:647-52.

Fick, A., *Über die Messung des Blutquantums in den Herzventrikeln*, Sitzungsbericht der Physikalisch-Medizinischen Gesellschaft zu Würzburg (1870) 36 (2 pages).

Gama de Abreu, Marcelo, et al., *Measurement of Pulmonary Capillary Blood Flow for Trending Mixed Venous Blood Oxygen Saturation and Oxygen Delivery*, Crit. Care Med. (1998), vol. 26, No. 1 (Suppl.), A106, Abstract #238, (1 page).

Gama de Abreu, Marcelo, et al., *Is the Partial $CO_2$ Rebreathing Technique a Useful Tool for Trending Pulmonary Capillary Blood Flow During Adjustments of Peep?*, Crit. Care Med. (1998), vol. 26, No. 1 (Suppl.), A106, Abstract #237, (1 page).

Gama de Abreu, et al., *Partial carbon dioxide rebreathing: A reliable technique for noninvasive measurement of nonshunted pulmonary capillary blood flow*, Crit. Care Med. (1997) 25(4):675-83.

Gedeon, A., et al., *Noninvasive Cardiac Output Determined with a New Method Based on Gas Exchange Measurements and Carbon Dioxide Rebreathing: A Study in Animals/Pigs*, J. Clin. Monit. (1992) 8(4):267-78.

Gedeon, A., et al., *A new method for noninvasive bedside determination of pulmonary blood flow*, Med. & Biol. Eng. & Comput. (1980) 18:411-418.

Guyton, A.E., et al., *Measurement of cardiac output by the direct Fick method*, In: Cardiac output and its regulation, W.B. Saunders Company (1973) 21-39.

International Search Report of Dec. 8, 2000.

Kyoku, I., et al. *Measurement of cardiac output by Fick method using $CO_2$ analyzer Servo*, Kyobu Geka. Japanese Journal of Thoracic Surgery (1988) 41(12):966-70.

Lynch, J., et al., *Comparison of a modified Fick method with thermodilution for determining cardiac output in critically ill patients on mechanical ventilation*, Intensive Care Med. (1990) 16:248-51.

Mahutte, C. Kees, et al., *Relationship of Thermodilution Cardiac Output to Metabolic Measurements and Mixed Venous Oxygen Saturation*, Chest (1993) 104(4):1236-42.

Miller, D.M., et al., *A Simple Method for the Continuous Noninvasive Estimate of Cardiac Output Using the Maxima Breathing System. A Pilot Study*, Anaesth. Intens. Care (1997) 25(1):23-28.

Österlund, B., et al., *A new method of using gas exchange measurements for the noninvasive determination of cardiac output: clinical experiences in adults following cardiac surgery*, Acta Anaesthesiol Scand (1995) 39:727-32.

Sackner, Marvin A., *Measurement of cardiac output by alveolar gas exchange*, Handbook of Physiology~The Respiratory System IV, Chapter 13, 233-55. (1987).

Spalding, H. K., et al., *Carbon Dioxide ($CO_2$) Elimination Rate Accurately Predicts Cardiac Output*, Anesthesiology (1997) 87(3A) (1 page).

Sprung, Charles L., et al., *Ventricular Arrhythmias During Swan-Ganz Catheterization of the Critically Ill*, Chest (1981) 79:413-15.

Taskar, V., et al., *Dynamics of Carbon Dioxide Elimination Following Ventilator Resetting*, Chest (1995) 108:196-202.

Winkler, Tilo, et al., *Pulmonary Capillary Blood Flow by Partial $CO_2$ Rebreathing: A Simulation Study Using a Bicompartmental Model of Gas Exchange*, Crit. Care Med. (1998), vol. 26, No. 1 (Suppl.), A105, Abstract #234, (1 page).

SYSTEMS AND METHODS FOR ACCURATELY, SUBSTANTIALLY NONINVASIVELY DETERMINING PULMONARY CAPILLARY BLOOD FLOW OR CARDIAC OUTPUT

CROSS-REFERENCE TO RELATED APPLICATIONS

This application is a continuation of application Ser. No. 10/400,717, filed Mar. 27, 2003, now U.S. Pat. No. 7,025,731, which is a continuation of application Ser. No. 09/510,702, filed Feb. 22, 2000, now U.S. Pat. No. 6,540,689, issued on Apr. 1, 2003.

BACKGROUND OF THE INVENTION

1. Field of the Invention

The present invention relates to methods for accurately, noninvasively measuring the pulmonary capillary blood flow (PCBF), cardiac output, and mixed venous carbon dioxide content of the blood of a patient. Particularly, the present invention relates to a method for noninvasively measuring pulmonary capillary blood flow or cardiac output that employs an algorithm to increase the accuracy of data upon which the pulmonary capillary blood flow or cardiac output measurement is based.

2. State of the Art

Carbon dioxide elimination ($V_{CO_2}$) is the volume of carbon dioxide ($CO_2$) excreted from the body of a patient during respiration. Conventionally, carbon dioxide elimination has been employed as an indicator of metabolic activity. Carbon dioxide elimination has also been used in rebreathing methods of determining pulmonary capillary blood flow and cardiac output.

The carbon dioxide Fick equation:

$$Q = V_{CO_2}/(CvCO_2 - CaCO_2), \quad (1)$$

where Q is cardiac output, $CvCO_2$ is carbon dioxide content of the venous blood of the patient, and $CaCO_2$ is the carbon dioxide content of the arterial blood of the patient, has been employed to noninvasively determine the pulmonary capillary blood flow or cardiac output of a patient. The carbon dioxide elimination of the patient may be noninvasively measured as the difference per breath between the volume of carbon dioxide inhaled during inspiration and the volume of carbon dioxide exhaled during expiration, and is typically calculated as the integral of the carbon dioxide signal, or the fraction of respiratory gases that comprises carbon dioxide, or "carbon dioxide fraction," times the rate of flow over an entire breath.

The partial pressure of end-tidal carbon dioxide ($PetCO_2$ or $etCO_2$) is also measured in rebreathing processes. The partial pressure of end-tidal carbon dioxide, after correcting for any deadspace, is typically assumed to be approximately equal to the partial pressure of carbon dioxide in the alveoli ($P_ACO_2$) of the patient or, if there is no intrapulmonary shunt, the partial pressure of carbon dioxide in the arterial blood of the patient ($PaCO_2$).

Rebreathing is typically employed either to noninvasively estimate the carbon dioxide content of mixed venous blood (as in total rebreathing) or to obviate the need to know the carbon dioxide content of the mixed venous blood (by partial rebreathing). Rebreathing processes typically include the inhalation of a gas mixture that includes carbon dioxide. During rebreathing, the carbon dioxide elimination of the patient decreases to a level less than during normal breathing. Rebreathing during which the carbon dioxide elimination decreases to near zero is typically referred to as total rebreathing. Rebreathing that causes some decrease, but not a total cessation of carbon dioxide elimination, is typically referred to as partial rebreathing.

Rebreathing is typically conducted with a rebreathing circuit, which causes a patient to inhale a gas mixture that includes carbon dioxide. FIG. 1 schematically illustrates an exemplary rebreathing circuit 50 that includes a tubular airway 52 that communicates air flow to and from the lungs of a patient. Tubular airway 52 may be placed in communication with the trachea of the patient by known intubation processes, or by connection to a breathing mask positioned over the nose and/or mouth of the patient. A flow meter 72, which is typically referred to as a pneumotachometer, and a carbon dioxide sensor 74, which is typically referred to as a capnometer, are disposed between tubular airway 52 and a length of hose 60 and are exposed to any air that flows through rebreathing circuit 50. Both ends of another length of hose, which is referred to as deadspace 70, communicate with hose 60. The two ends of deadspace 70 are separated from one another by a two-way valve 68, which may be positioned to direct the flow of air through deadspace 70. Deadspace 70 may also include an expandable section 62. A Y-piece 58, disposed on hose 60 opposite flow meter 72 and carbon dioxide sensor 74, facilitates the connection of an inspiratory hose 54 and an expiratory hose 56 to rebreathing circuit 50 and the flow communication of the inspiratory hose 54 and expiratory hose 56 with hose 60. During inhalation, gas flows into inspiratory hose 54 from the atmosphere or a ventilator (not shown). During normal breathing, valve 68 is positioned to prevent inhaled and exhaled air from flowing through deadspace 70. During rebreathing, valve 68 is positioned to direct the flow of exhaled and inhaled gases through deadspace 70.

The rebreathed air, which is inhaled from deadspace 70 during rebreathing, includes air that has been exhaled by the patient (i.e., carbon dioxide-rich air).

During total rebreathing, substantially all of the gas inhaled by the patient was expired during the previous breath. Thus, during total rebreathing, the partial pressure of end-tidal carbon dioxide ($PetCO_2$ or $etCO_2$) is typically assumed to be equal to or closely related to the partial pressure of carbon dioxide in the arterial ($PaCO_2$), venous ($PvCO_2$), or alveolar ($P_ACO_2$) blood of the patient. Total rebreathing processes are based on the assumption that neither pulmonary capillary blood flow nor the content of carbon dioxide in the venous blood of the patient ($CvCO_2$) changes substantially during the rebreathing process. The partial pressure of carbon dioxide in blood may be converted to the content of carbon dioxide in blood by means of a carbon dioxide dissociation curve, where the change in the carbon dioxide content of the blood ($CvCO_2 - CaCO_2$) is equal to the slope (s) of the carbon dioxide dissociation curve multiplied by the measured change in end-tidal carbon dioxide ($PetCO_2$) as effected by a change in effective ventilation, such as rebreathing.

In partial rebreathing, the patient inhales a mixture of "fresh" gases and gases exhaled during the previous breath. Thus, the patient does not inhale a volume of carbon dioxide as large as the volume of carbon dioxide that would be inhaled during a total rebreathing process. Conventional partial rebreathing processes typically employ a differential form of the carbon dioxide Fick equation to determine the pulmonary capillary blood flow or cardiac output of the patient, which do not require knowledge of the carbon dioxide content of the mixed venous blood. This differential form of the carbon dioxide Fick equation considers measurements of carbon dioxide elimination, $CvCO_2$, and the content of carbon dioxide in the alveolar blood of the patient ($C_ACO_2$) during both normal breathing and the rebreathing process as follows:

$$Q_{pcbfBD} = \frac{V_{CO_{2B}} - V_{CO_{2D}}}{(CvCO_{2B} - CvCO_{2D}) - (CaCO_{2B} - CaCO_{2D})}, \quad (2)$$

where $V_{CO_2 B}$ and $V_{CO_2 D}$ are the carbon dioxide production of the patient before rebreathing and during the rebreathing process, respectively, $CvCO_{2 B}$ and $CvCO_{2 D}$ are the content of $CO_2$ of the venous blood of the patient before rebreathing and during the rebreathing process, respectively, and $CaCO_{2 B}$ and $CaCO_{2 D}$ are the content of $CO_2$ in the arterial blood of the patient before rebreathing and during rebreathing, respectively.

Again, with a carbon dioxide dissociation curve, the measured $PetCO_2$ can be used to determine the change in content of carbon dioxide in the blood before and during the rebreathing process. Accordingly, the following equation can be used to determine pulmonary capillary blood flow or cardiac output when partial rebreathing is conducted:

$$Q = \Delta V_{CO_2}/s\Delta PetCO_2. \quad (3)$$

Alternative differential Fick methods of measuring pulmonary capillary blood flow or cardiac output have also been employed. Such differential Fick methods typically include a brief change of $PetCO_2$ and $V_{CO_2}$ in response to a change in effective ventilation. This brief change can be accomplished by adjusting the respiratory rate, inspiratory and/or expiratory times, or tidal volume. A brief change in effective ventilation may also be effected by adding $CO_2$, either directly or by rebreathing. An exemplary differential Fick method that has been employed, which is disclosed in Gedeon, A. et al. in 18 *Med. &Biol. Eng. &Comput.* 411-418 (1980), employs a period of increased ventilation followed immediately by a period of decreased ventilation.

The carbon dioxide elimination of a patient is typically measured over the course of a breath by the following, or an equivalent, equation:

$$V_{CO_2} = \int_{breath} V \times f_{CO_2} dt, \quad (4)$$

where V is the measured respiratory flow and $f_{CO_2}$ is the substantially simultaneously detected carbon dioxide signal, or fraction of the respiratory gases that comprises carbon dioxide or "carbon dioxide fraction."

Due to the measured respiratory constituents upon which $V_{CO_2}$ and $PetCO_2$ calculations are made, $V_{CO_2}$ typically responds to rebreathing about one breath before $PetCO_2$ for the same breath. Accordingly, a $V_{CO_2}$ signal may lead a $PetCO_2$ signal by about one breath. Thus, at a particular point in time, the $V_{CO_2}$ and $PetCO_2$ signals do not correspond to one another. As these values are often used to noninvasively determine pulmonary capillary blood flow or cardiac output, the lack of correspondence between these values may lead to inaccuracies in the pulmonary capillary blood flow or cardiac output determination.

In addition, measurements that are taken during spurious breaths, or breaths which do not provide information relevant to pulmonary capillary blood flow or cardiac output, may act as noise that introduces inaccuracy into the noninvasive pulmonary capillary blood flow or cardiac output determination.

When equation (4) is employed to calculate the carbon dioxide elimination of the patient from the respiratory flow and carbon dioxide fraction measurements over an entire breath, such miscorrelation or noise-induced inaccuracies in either the expiratory flow, the inspiratory flow, or both may cause inaccuracies in the carbon dioxide elimination determination or inconsistencies between carbon dioxide elimination determinations.

Accordingly, there is a need for a method of accurately, noninvasively calculating pulmonary capillary blood flow and cardiac output.

SUMMARY OF THE INVENTION

The present invention includes a method for noninvasively measuring pulmonary capillary blood flow and cardiac output. The present invention includes the use of known rebreathing techniques to substantially noninvasively obtain carbon dioxide elimination ($V_{CO_2}$) and partial pressure of end-tidal carbon dioxide ($PetCO_2$) measurements of a patient's breathing. These measurements may then be used to calculate pulmonary capillary blood flow or cardiac output of the patient by employing the following equation:

$$Q = \frac{\Delta V_{CO_2}}{\Delta CaCO_2} = \frac{\Delta V_{CO_2}}{s\Delta PetCO_2}, \quad (5)$$

where s is the slope of a standard carbon dioxide ($CO_2$) dissociation curve, $\Delta V_{CO_2}$ is the change in the carbon dioxide elimination of the patient due to a change in effective ventilation, such as that caused by rebreathing, and $\Delta CaCO_2$ and $\Delta PetCO_2$ are the change in the content of carbon dioxide in the arterial blood of the patient and the change in the end-tidal partial pressure of carbon dioxide of the patient, respectively, due to the same change in effective ventilation. Alternatively, a standard carbon dioxide dissociation curve can be used to determine $\Delta CaCO_2$ on the basis of the measured $\Delta PetCO_2$.

As an alternative to the use of the above equations to determine pulmonary capillary blood flow or cardiac output, the substantially noninvasive $V_{CO_2}$ and $CaCO_2$ measurements can be related to each other in a linear fashion. This can be visually diagrammed by plotting the $V_{CO_2}$ and $CaCO_2$ measurements against one another on a two-dimensional (X-Y) line graph. The negative slope (−1×m) of the best-fit line through the data is approximately equal to the pulmonary capillary blood flow. The appropriate location and orientation of such a best-fit line may be calculated by linear regression or least squares. Depending on the correlation between the calculated best-fit line and the measured data, it may also be desirable to modify the data to provide a best-fit line that closely corresponds to the data.

In one embodiment of the method of the present invention, the data can be modified by use of a known filter, such as a low-pass filter or a high-pass filter. Either digital or analog filters may be used. Either linear or nonlinear (e.g., median) filters may be used. By way of example, and not to limit the scope of the present invention, a low-pass filter may be applied to the measured $V_{CO_2}$ signal. As another example, a high-pass filter may be applied to the measured $CaCO_2$ signal. Preferably, the filter and filter coefficient that are selected maximize the correlation between the measured $V_{CO_2}$ and $CaCO_2$ signals.

In another embodiment of the method of the present invention, the data points can be modified by clustering. That is, the data points that are grouped closest to other data points are assumed to most accurately represent the true $V_{CO_2}$ and $CaCO_2$ of the patient. For example, the measured data with at least a predetermined number of close, or similar (e.g., within a specified threshold), data points is retained, while measured data with less than the predetermined number of close data points is discarded. The retained data points are assumed to be located on or near the best-fit line. In clustering, only these closely grouped sets of data points are considered in recalculating the best-fit line for the data and, thus, the negative slope (i.e., −1×m) of the best-fit line to determine the pulmonary capillary blood flow or cardiac output of the patient.

Another embodiment of the method of the present invention includes modifying the data points that are most likely to be closest to an accurately placed and oriented best-fit line. Each data point, which has a carbon dioxide elimination component (e.g., a y-ordinate component) and a component based on an indicator of carbon dioxide content (e.g., an x-ordinate component), is evaluated on the basis of a predetermined minimum expected pulmonary capillary blood flow and a predetermined maximum pulmonary capillary blood flow. Lines, or the equations therefor, for both minimum expected and maximum expected pulmonary capillary blood flows are located so as to intersect at each data point. Then, the number of the other data points that are located between the two pulmonary capillary blood flow lines or equations is determined for each data point. Only those data points with a threshold number of other data points between the two intersecting lines are used in the determination of the location and orientation of the best-fit line through the data.

Of course, any combination of methods of modifying data may be used to accurately determine the slope of the best-fit line through the measured $V_{CO_2}$ and $PetCO_2$ data and, thus, to determine the pulmonary capillary blood flow or cardiac output of a patient.

The best-fit line through carbon dioxide elimination and carbon dioxide content data may also be used to determine the mixed venous carbon dioxide content of the patient when partial rebreathing techniques are employed to obtain the data. As the mixed venous carbon dioxide content is assumed to equal the carbon dioxide content of the patient's blood when carbon dioxide elimination ceases (which does not occur during partial rebreathing), a best-fit line obtained by use of partial rebreathing techniques can be used to noninvasively determine carbon dioxide content and, thus, mixed venous carbon dioxide content when carbon dioxide elimination is set at zero.

Other features and advantages of the present invention will become apparent to those of ordinary skill in the art through a consideration of the ensuing description, the accompanying drawings, and the appended claims.

DETAILED DESCRIPTION OF THE INVENTION

The present invention includes use of the Fick equation to calculate pulmonary capillary blood flow or cardiac output as the ratio of a change in carbon dioxide elimination, or $V_{CO_2}$, to a change in the content of carbon dioxide, or $CaCO_2$, in the arterial blood of a patient:

$$Q = \frac{\Delta V_{CO_2}}{\Delta CaCO_2}. \tag{6}$$

$CaCO_2$, or the content of carbon dioxide in the arterial blood of a patient, can be noninvasively estimated by determining the $PetCO_2$, or partial pressure of carbon dioxide in the end-tidal respiration of a patient, and converting $PetCO_2$ to $CaCO_2$ by use of a standard carbon dioxide dissociation curve, as is known in the art, as follows:

$$\Delta CaCO_2 = s\Delta PetCO_2, \tag{7}$$

where s is the slope of the carbon dioxide dissociation curve and $\Delta PetCO_2$ is a change in the end-tidal partial pressure of carbon dioxide of a patient effected by a change in ventilation. Thus, pulmonary capillary blood flow or cardiac output can also be calculated as follows:

$$Q = \Delta V_{CO_2}/s\Delta PetCO_2, \tag{8}$$

Other indicators of the carbon dioxide content in the blood of a patient, such as $pCO_2$, may be used in place of $PetCO_2$ or $CaCO_2$ to determine the pulmonary capillary blood flow or cardiac output of a patient.

$V_{CO_2}$ and $PetCO_2$, $CaCO_2$, $pCO_2$, or other indicators of the carbon dioxide content in the blood of a patient can be calculated or determined on the basis of substantially noninvasively obtained respiratory flow and respiratory carbon dioxide pressure data.

Figure 2:
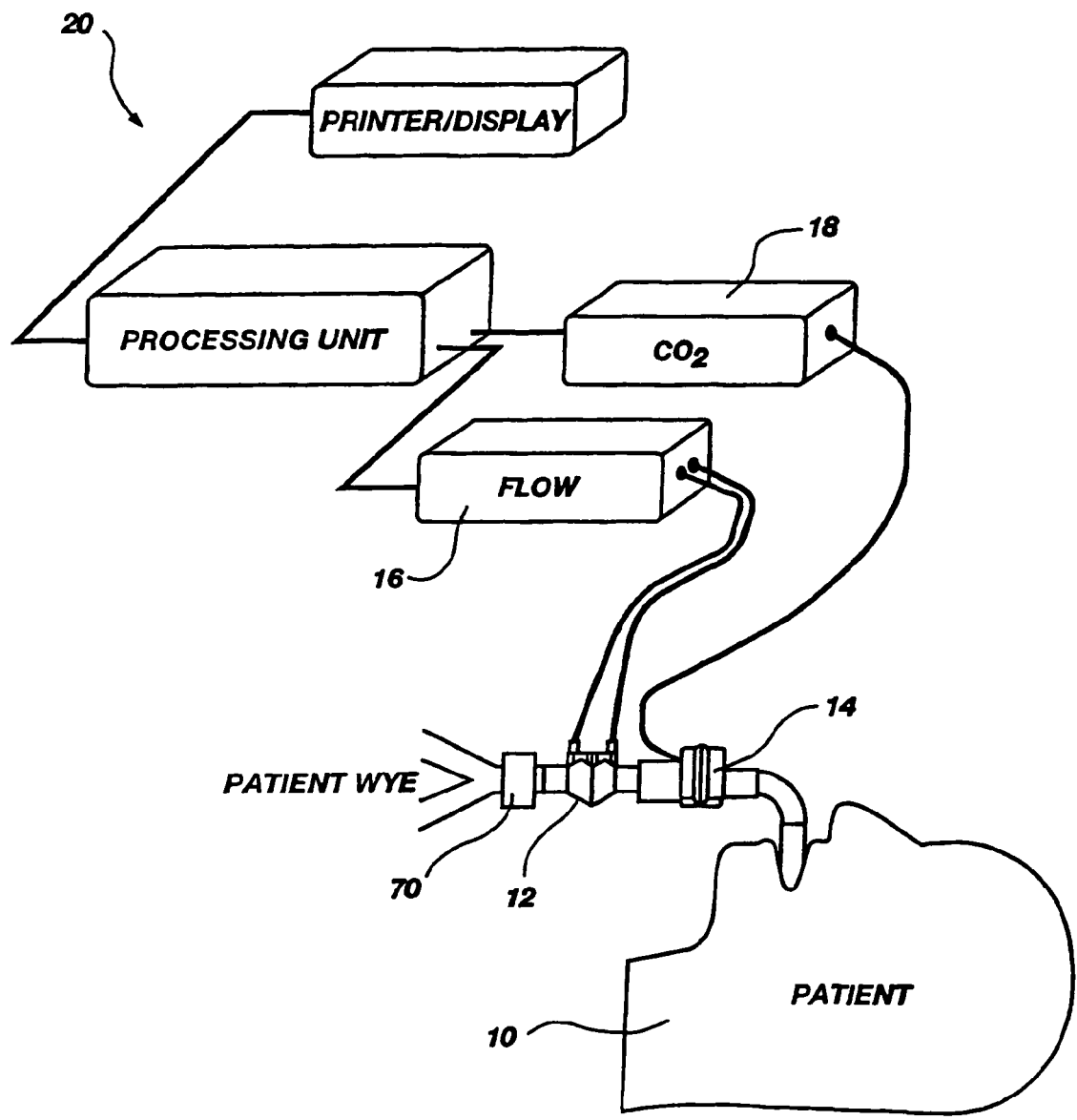
FIG. 2 is a schematic representation which illustrates the componentry that may be utilized to measure respiratory profile parameters that are employed in the methods of the present invention.

FIG. 2 schematically illustrates an exemplary method of substantially noninvasively monitoring the respiration of a patient and of measuring the flow rates and carbon dioxide concentration of gas mixtures that are inhaled and exhaled by a patient 10 over the course of the patient's breathing, such as during normal respiration or during known rebreathing techniques. A flow sensor 12 of a known type, such as the differential-pressure type respiratory flow sensors manufactured by Novametrix Medical Systems Inc. ("Novametrix") of Wallingford, Conn. (e.g., the Pediatric/Adult Flow Sensor (Catalog No. 6717) or the Neonatal Flow Sensor (Catalog No. 6718)), which may be operatively attached to a ventilation apparatus (not shown), as well as respiratory flow sensors based on other operating principles and manufactured or marketed by others, may be employed to measure the flow rates of the breathing of patient 10.

A carbon dioxide sensor 14, such as the CAPNOSTAT® carbon dioxide sensor and a complementary airway adapter (e.g., the Pediatric/Adult Single Patient Use Airway Adapter (Catalog No. 6063), the Pediatric/Adult Reusable Airway Adapter (Catalog No. 7007), or the Neonatal/Pediatric Reusable Airway Adapter (Catalog No. 7053)), which are manufactured by Novametrix, as well as main stream and side stream carbon dioxide sensors manufactured or marketed by others, may be employed to measure the carbon dioxide concentration of gas mixtures that are inhaled and exhaled by patient 10.

Flow sensor 12 and carbon dioxide sensor 14 are connected to a flow monitor 16 and a carbon dioxide monitor 18, respectively, each of which may be operatively associated with a computer 20 so that data from the flow and carbon dioxide monitors 16 and 18 representative of the signals from each of flow sensor 12 and carbon dioxide sensor 14 may be detected by computer 20 and processed according to programming (e.g., by software) thereof. Preferably, raw flow and carbon dioxide signals from the flow monitor and carbon dioxide sensor are filtered to remove any significant artifacts. As respiratory flow and carbon dioxide pressure measurements are made, the respiratory flow and carbon dioxide pressure data may be stored by computer 20.

Each breath, or breathing cycle, of patient 10 may be delineated as known in the art, such as by continuously monitoring the flow rate of the breathing of patient 10.

Figure 1:
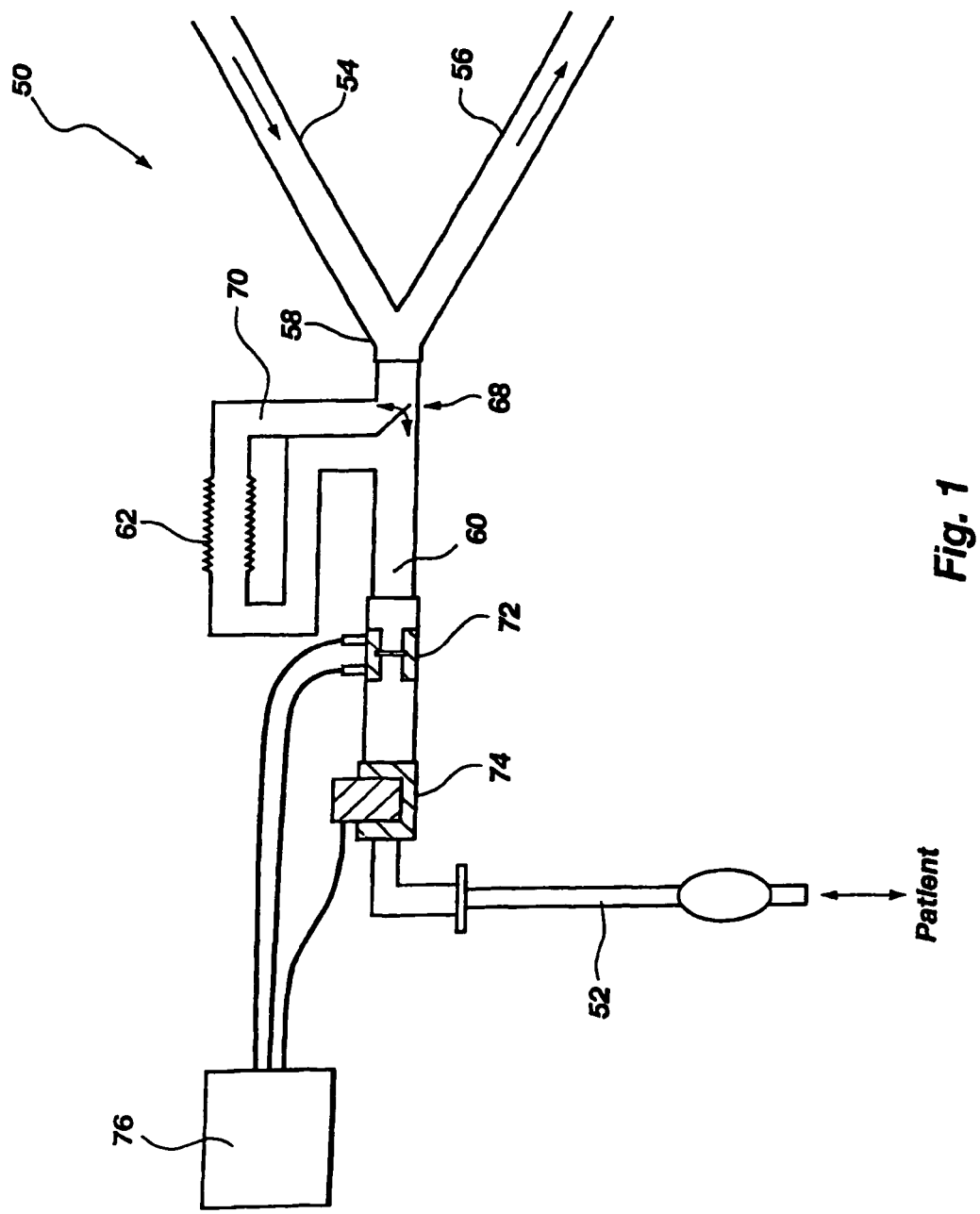
FIG. 1 is a schematic representation of an exemplary rebreathing circuit that may be employed with the methods of the present invention.
Figure 3A:
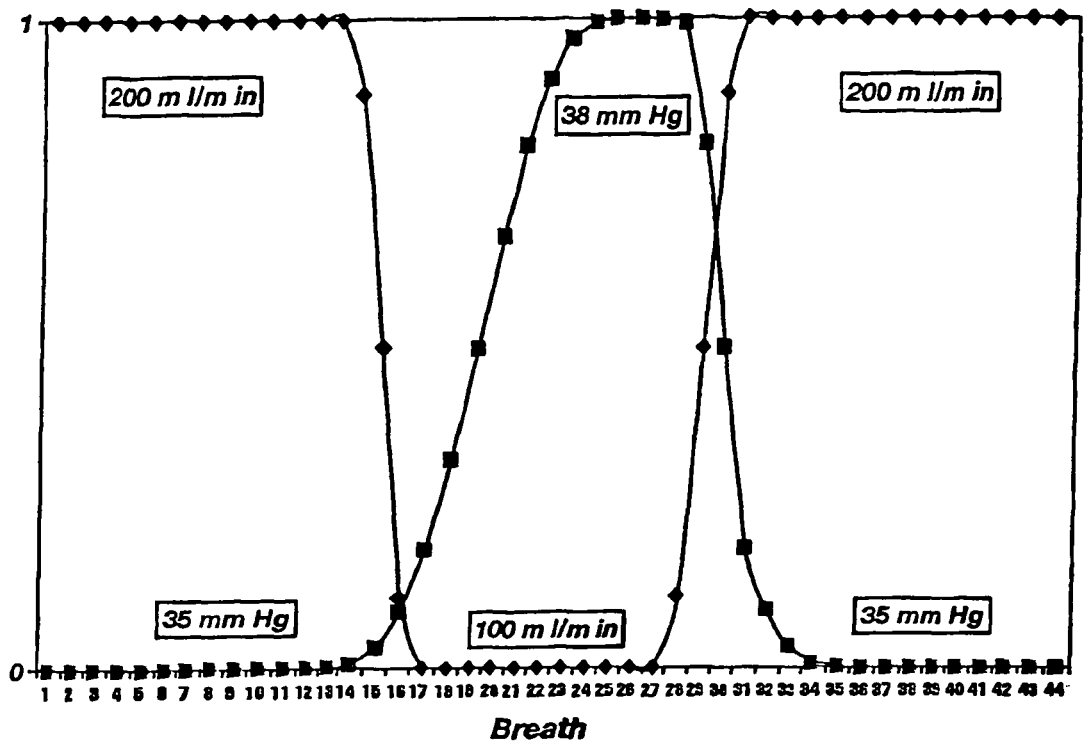
FIG. 3A illustrates an idealized, bidirectional rebreathing cycle with $V_{CO_2}$ values for different breaths depicted as diamonds and $PetCO_2$ values for various breaths shown as squares.

As use of the Fick equation to calculate pulmonary capillary blood flow or cardiac output requires that a change in $V_{CO_2}$ and $CaCO_2$, $PetCO_2$, $pCO_2$ or another indicator of the carbon dioxide content in the blood of a patient be known, a change in effective ventilation is required. By way of example, and not to limit the scope of the present invention, rebreathing techniques, such as by use of a dead space 70 such as that provided by the rebreathing circuit illustrated in FIG. 1, may be employed to cause a change in effective ventilation. FIG. 3A illustrates the changes that may occur when a bidirectional rebreathing process, such as that disclosed in U.S. patent application Ser. No. 09/150,136, filed Sep. 9, 1998, and assigned to the same assignee as the present invention, is used to effect a change in effective ventilation. The graph of FIG. 3A illustrates the typical changes in the $V_{CO_2}$ (shown as diamonds) and carbon dioxide content measurements (e.g., $PetCO_2$, shown as squares) that may occur between the baseline breathing (i.e., before rebreathing), during rebreathing, and the stabilization (i.e., after rebreathing) periods of an idealized (i.e., without noise) bidirectional rebreathing cycle. During rebreathing, $V_{CO_2}$ changes from a baseline value (e.g., about 200 ml/min) to a during rebreathing plateau (e.g., of about 100 ml/min.) within about 3 or 4 breaths, whereas carbon dioxide content may take longer to change from a baseline value (e.g., 38 mmHg) to a plateau (e.g., about 35 mmHg).

Figure 3B:
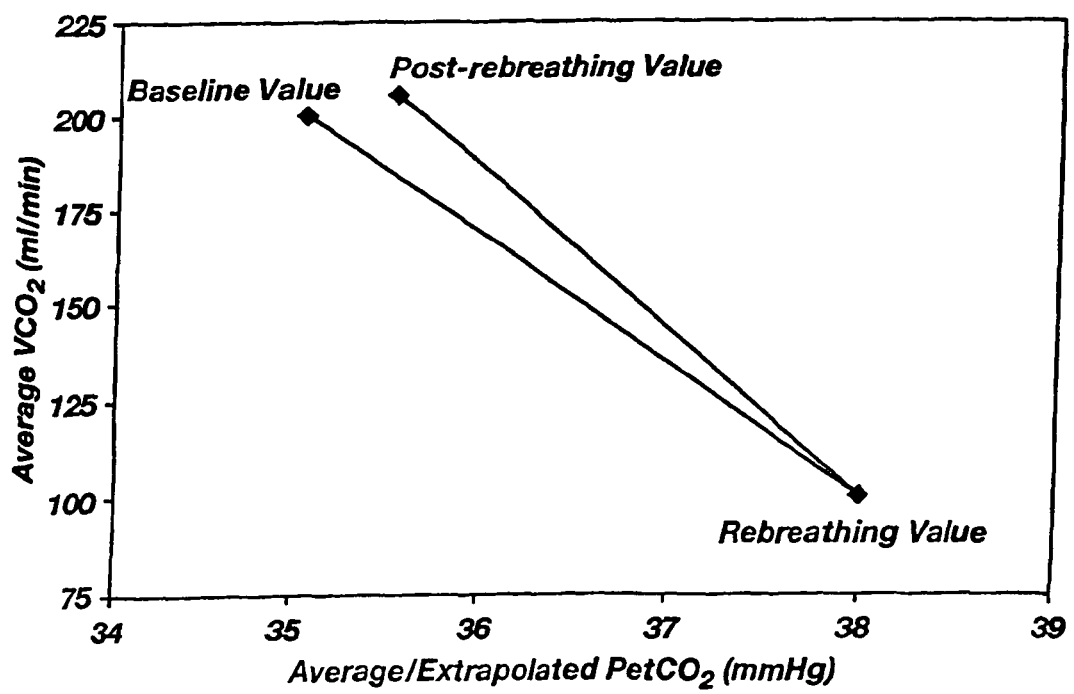
FIG. 3B is a two-dimensional plot illustrating the use of a known, bidirectional rebreathing process to obtain three $V_{CO_2}$ values and three values representative of the carbon dioxide content of the blood of a patient before, during, and after rebreathing; these three values have been used to substantially noninvasively determine the pulmonary capillary blood flow or cardiac output of the patient.

FIG. 3B is a two-dimensional plot illustrating that one value, the plateau value, from each of the before, during, and after rebreathing phases of a bidirectional rebreathing process, such as that illustrated in FIG. 3A, was used to estimate pulmonary capillary blood flow or cardiac output. By way of contrast, in a method of determining pulmonary capillary blood flow or cardiac output incorporating teachings of the present invention, $V_{CO_2}$ and carbon dioxide content data are continually measured, providing a plot such as that shown in FIG. 3C, with data at 100 being based on before rebreathing measurements, data along arrow 102 being based on during rebreathing measurements, and data along arrow 104 being based on after rebreathing measurements. These data may be obtained by use of a single rebreathing cycle, over the course of a number of rebreathing cycles, at one or more discrete time intervals, or on a breath-by-breath basis, where data is continually measured, calculated, and analyzed in accordance with the method of the invention so as to continually update or monitor the pulmonary capillary blood flow or cardiac output of a patient.

When rebreathing or other known techniques are used to cause a change in effective ventilation so as to facilitate the substantially noninvasive determination of pulmonary capillary blood flow or cardiac output, respiratory flow and carbon dioxide pressure data are obtained during at least the before, during, and after stages of rebreathing. Total or partial rebreathing processes may be used in the method of the present invention. These respiratory flow and carbon dioxide pressure data are then used, as known in the art, to calculate $V_{CO_2}$ and $PetCO_2$, as well as the changes in $V_{CO_2}$ and $PetCO_2$ that occur with the change in effective ventilation.

The calculated $V_{CO_2}$ and $PetCO_2$ data are then used to determine the pulmonary capillary blood flow or cardiac output of the patient, such as by use of the Fick equations presented above.

As an alternative, the pulmonary capillary blood flow or cardiac output of a patient can be determined over the course of a plurality of breaths by expressing the calculated $V_{CO_2}$ data and $CaCO_2$ data or data of another indicator of the content of carbon dioxide in the blood of a patient, such as $PetCO_2$ or $pCO_2$, in two dimensions, such as on a two-dimensional (X-Y) line graph, with $V_{CO_2}$ data points being measured on the y-axis and $PetCO_2$ data points being measured on the x-axis, then identifying a line that best fits the data, which is also referred to herein as a best-fit line.

For example, the equation for the best-fit line is:

$$y = mx + b \qquad (9)$$

or $$m = \frac{y-b}{x}, \qquad (10)$$

where y is the y-axis coordinate of a data point, x is the x-axis coordinate of the same data point, m is the slope of the line, and b is the offset value for the line. If $V_{CO_2}$ is measured on the y-axis and $CaCO_2$ is measured on the x-axis, then $$m = \frac{V_{CO_2} - b}{CaCO_2}. \qquad (11)$$

The negative slope (i.e., $-1 \times m$) of the best-fit line through the $V_{CO_2}$—$CaCO_2$ data would be equal to the pulmonary capillary blood flow or cardiac output of the patient:

$$-m = Q. \qquad (12)$$

The best-fit line for the $V_{CO_2}$ and $CaCO_2$ data is preferably determined by use of known linear regression techniques or any other known methodology for determining the relationship between two variables. The method of linear regression provides an accurate pulmonary capillary blood flow or cardiac output value based on a large number of $V_{CO_2}$ and $CaCO_2$ data obtained over the course of one or more changes in effective ventilation. When linear regression is used, the slope (m) of the best-fit line for the data is calculated as follows:

$$m = Lxy/Lxx \quad (13)$$

and the offset (b) of the line is calculated by the following equation:

$$b = \Sigma y/n - m \times \Sigma x/n, \quad (14)$$

where $$Lxx = \Sigma x^2 - (\Sigma x \times \Sigma x)/n, \quad (15)$$

$$Lyy = \Sigma y^2 - (\Sigma y \times \Sigma y)/n, \text{ and} \quad (16)$$

$$Lxy = \Sigma xy - (\Sigma x \times y)/n, \quad (17)$$

and where n is the number of data points in the plot, $\Sigma x$ is the sum of all x-coordinate (i.e., $CaCO_2$ content) values, $\Sigma y$ is the sum of all y-coordinate (i.e., $V_{CO_2}$) values, $\Sigma x^2$ is the sum of the square of all x-coordinate values, $\Sigma y^2$ is the sum of the square of all y-coordinate values, and $\Sigma xy$ is the sum all paired x- and y-coordinate values multiplied by each other.

When linear regression is used to determine the location and orientation of a best-fit line, a correlation coefficient (r) that quantifies the accuracy with which the best-fit line correlates to the $V_{CO_2}$ and $CaCO_2$ data can also be calculated as follows:

$$r = (Lxy \times Lxy)/(Lyy \times Lxx). \quad (18)$$

Alternatively, any other measure of the quality of fit that quantifies the accuracy with which the best-fit line correlates to the $V_{CO_2}$ and $CaCO_2$ data may be used.

Correlation coefficients range from 0 to 1.0, where a correlation coefficient of 0 indicates that no linear correlation exists between the x-ordinate and the y-ordinate data and a correlation coefficient of 1.0 indicates that the x-ordinate and y-ordinate data are perfectly linearly correlated (i.e., all of the $V_{CO_2}$-$aCO_2$ data points are located on the same straight line).

Figure 3C:
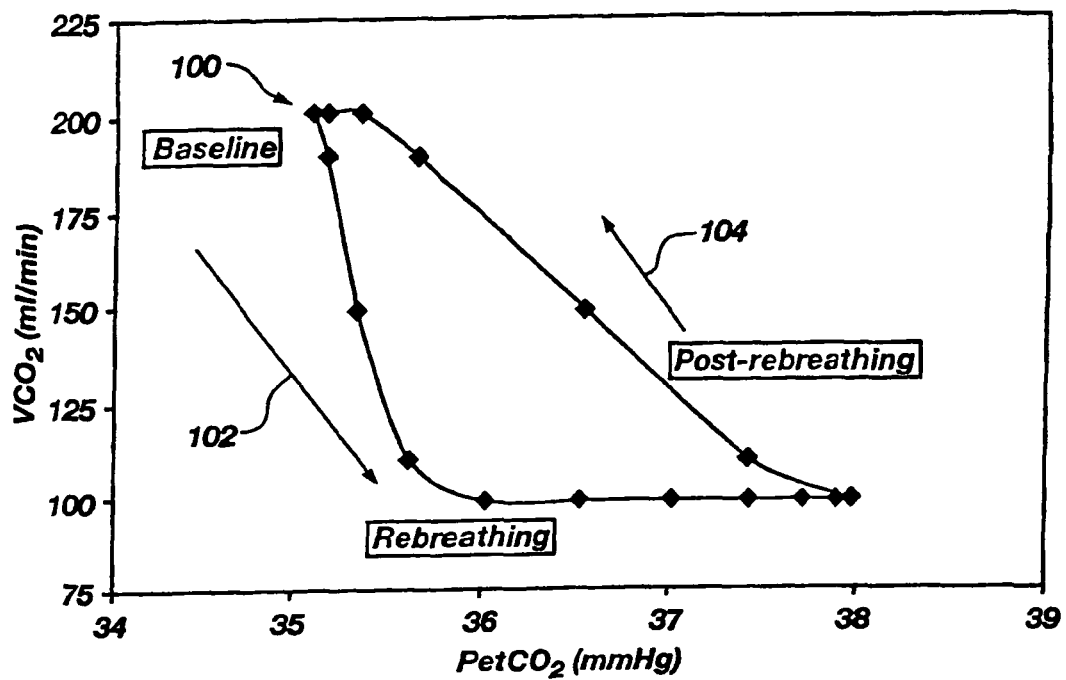
FIG. 3C is a two-dimensional plot of a number of $V_{CO_2}$ values against the same number of carbon dioxide content values obtained over a single bidirectional rebreathing cycle.
Figure 5:
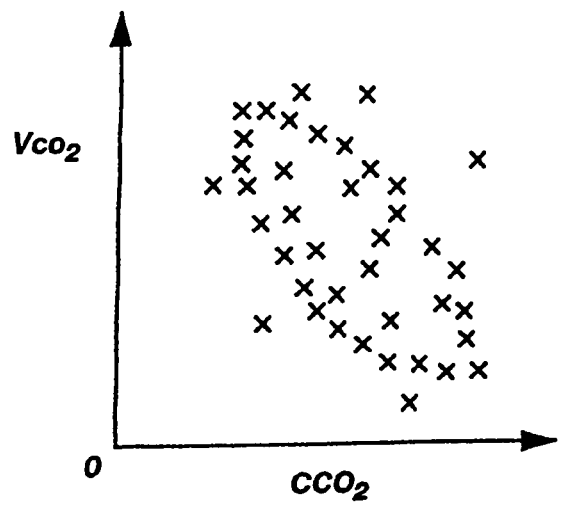
FIG. 5 is a two-dimensional line graph illustrating a typical plot of $V_{CO_2}$ on the y-axis and $CaCO_2$ on the x-axis.

The $V_{CO_2}$—$CaCO_2$ data points measured before and during rebreathing, however, are rarely located on the same straight line. One reason for this is that, during rebreathing maneuvers, the $V_{CO_2}$ signal typically leads the $PetCO_2$ signal and, thus, the $CaCO_2$ by about one breath. In addition, $V_{CO_2}$ is calculated on the basis of signal components that have higher frequencies than do the $PetCO_2$ signal. As a result, when the $V_{CO_2}$ and $CaCO_2$ measurements calculated over a period of time are plotted against one another on a two-dimensional (X-Y) line graph, the result typically appears as an arc or a loop, as shown in FIGS. 3C and 5, rather than as a straight line, depending on the amount of data calculated and the duration of rebreathing. Moreover, $V_{CO_2}$ and $CaCO_2$ measurements may be calculated on the basis of respiratory flow and carbon dioxide pressure data obtained during spurious breaths. Such data do not relate to the pulmonary capillary blood flow or cardiac output measurement. $V_{CO_2}$ and $CaCO_2$ calculations that are based upon such spurious data act as noise that may result in miscalculation of a best-fit line through the calculated $V_{CO_2}$ and $CaCO_2$ data. As a result, the correlation coefficient of a best-fit line to the data is typically much less than 1.0.

The measured respiratory flow and carbon dioxide pressure data or the calculated $V_{CO_2}$ and $CaCO_2$ data can be modified to increase the correlation coefficient between the $V_{CO_2}$ and $CaCO_2$ data and the best-fit line therefor. Preferably, a linear transform is used to increase the correlation coefficient. A linear transform may be used to delay the calculation of a $V_{CO_2}$ data point to accurately coincide therewith a $CaCO_2$ data point based on measurements taken during the same breath. The measured or calculated data may also be filtered by use of a linear transform.

In one embodiment of a method for increasing the correlation coefficient between the $V_{CO_2}$ and $CaCO_2$ data and the best-fit line therefor, a filter is applied to the calculated $V_{CO_2}$ or $CaCO_2$ data. Known analog or digital low-pass, high-pass, or band pass filters, including adaptive filters, may be employed. Linear or nonlinear filters may be employed. Preferably, a first order (single pole) infinite impulse response (IIR) digital filter is employed to filter the $V_{CO_2}$ calculations in a manner that improves the correlation between the $V_{CO_2}$ calculation and the lagging $PetCO_2$/$CaCO_2$ calculation. The equation for such a filter is:

$$V_{CO_2}'[n] = \alpha \times V_{CO_2}'[n-1] + (1-\alpha) \times V_{CO_2}[n], \quad (19)$$

where $V_{CO_2}[n]$ is the most recently calculated, unfiltered $V_{CO_2}$ data point, $V_{CO_2}'[n-1]$ is the previous, filtered $V_{CO_2}$ data point, $V_{CO_2}'[n]$ is the new "filtered" value based on $V_{CO_2}[n]$ and obtained by use of the filter, and $\alpha$ is the filter coefficient. The filter coefficient, $\alpha$, has a range of 0 to 1.0. The greater the value of $\alpha$, the more profoundly the most recently calculated data point is filtered and, conversely, the lower $\alpha$ values cause the most recently calculated data points to be filtered to a lesser degree. When $\alpha$ is equal to zero, the most recently calculated data point is not filtered.

Due to anatomical and physiological differences between different patients, different patients have differing optimal filter coefficients, $\alpha$. In addition, as anatomical and physiological changes may occur in a patient over time, the optimum filter coefficients, $\alpha$, to be used in filtering the $V_{CO_2}$ or $CaCO_2$ values calculated from the patient's breathing may also vary over time. Accordingly, the selection of an optimal filter coefficient, $\alpha$, is also within the scope of the present invention. Any known optimization method or search algorithm may be employed to select the optimal filter coefficient, $\alpha$.

Figure 3D:
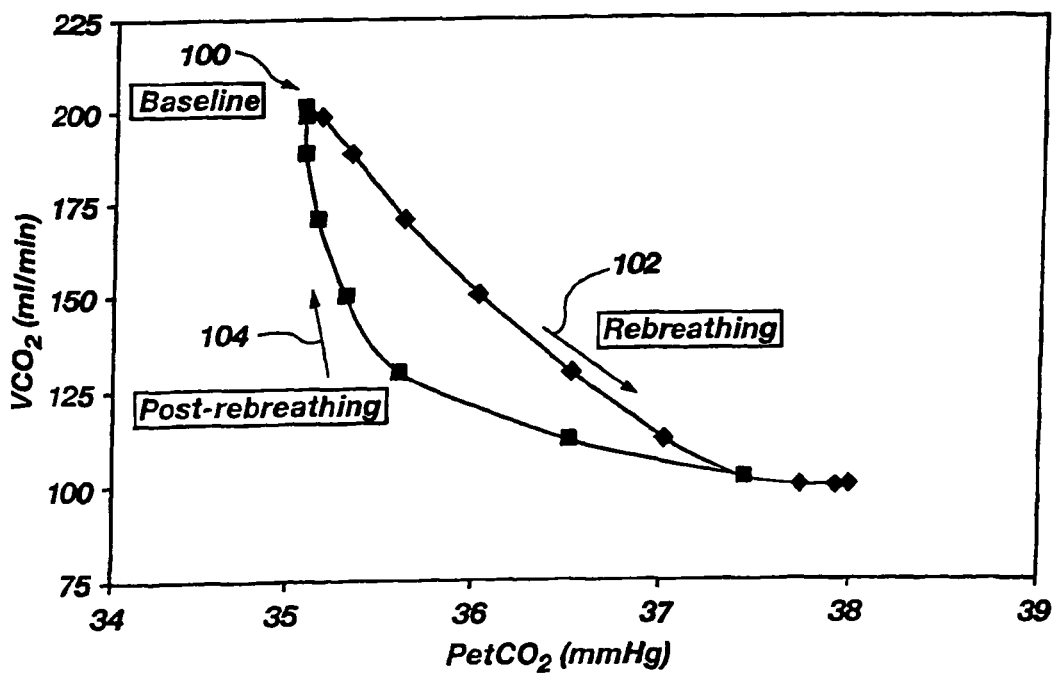
FIG. 3D is an exemplary two-dimensional plot depicting $V_{CO_2}$ and carbon dioxide content values from the same rebreathing cycle as that shown in FIG. 3C and modified in accordance with the method of the present invention.
Figure 6:
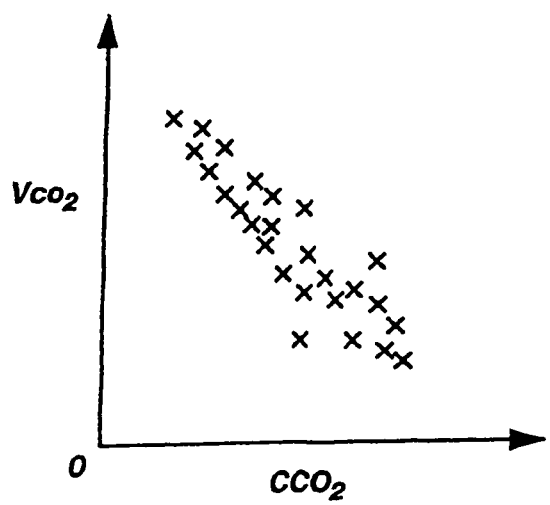
FIG. 6 is a two-dimensional line graph illustrating a plot of $V_{CO_2}$ on the y-axis and $CaCO_2$ on the x-axis after the $V_{CO_2}$ and $CaCO_2$ data have been modified in accordance with teachings of the present invention.

As an example of the way in which an optimal filter coefficient may be selected, $\alpha$ is first set to a default value (e.g., 0.85) and the calculated $V_{CO_2}$ or $CaCO_2$ values are filtered on the basis of the default filter coefficient, $\alpha$. The linear regression is then performed to obtain a best-fit line. If the correlation coefficient of best-fit line calculated with the just-filtered data is less than the correlation coefficient of the immediately preceding best-fit line, which was calculated with unfiltered data or with a prior filter coefficient, then a predetermined $\alpha$ adjustment value (e.g., 0.01) is changed by multiplying the a adjustment value by −1 and by modifying the filter coefficient by adding the modified a adjustment value thereto. Otherwise, the filter coefficient, $\alpha$, is modified by adding the unmodified a adjustment value thereto. The process of filtering the data based on a modified filter coefficient, obtaining a best-fit line for the data, comparing the correlation coefficient of the best-fit line to the correlation coefficient of the previous best-fit line, and adjusting the filter coefficient accordingly is then repeated a predetermined number of times (e.g., 50 times). The best-fit line with the greatest correlation coefficient, based on the unfiltered data and each set of filtered data, is selected to calculate the pulmonary capillary blood flow or cardiac output of the patient. When filtering is used, the $V_{CO_2}$—$CaCO_2$ plot preferably narrows, as depicted in FIGS. 3D and 6, to thereby increase the accuracy with which the location and orientation of a best-fit line can be established and, thus, to increase the accuracy of a pulmonary capillary blood flow or cardiac output determination based on the data.

Another embodiment of a method for increasing the correlation coefficient between the $V_{CO_2}$ and $CaCO_2$ data and the best-fit line therefor, which is referred to herein as "clustering," includes the selection of data points that are grouped closely together. That is, the data points that are selected include those data points having a number of other data points within a predetermined range thereof. Data points that are not clustered are probably inaccurate or based on measurements taken during spurious breaths. As an accurate best-fit line through the data would likely be based on the clustered data, the data points that are not located in a cluster are not used in calculating the location and orientation of a best-fit line for the data.

Clustering of the data points may include normalization or transformation of the data such that ranges of the x-coordinate data (e.g., the $CaCO_2$ data) and the y-coordinate data (e.g., the $V_{CO_2}$ data) are substantially the same. Without such normalization, the data group (e.g., the $V_{CO_2}$ data or the $CaCO_2$ data) with the highest range would dominate; the other data group would be less significant.

An exemplary manner in which the data may be normalized includes use of the following normalization:

$$x=(x-\bar{x})/\sigma_x, \quad (20)$$

where:

x is the raw value, $\bar{x}$ is the mean value of all x-axis (e.g., $CaCO_2$) data in the plot, and $\sigma_x$ is the standard deviation of all x-axis data in the plot. This normalization is applied to all x-axis values. A similar normalization scheme is applied to all of the y-axis values.

The normalized data may then be clustered by searching for a predetermined number (e.g., 5) of the closest data points (e.g., $V_{CO_2}$ or $CaCO_2$ data points) to each of the data points in a group. The differences between the analyzed data point and each of the predetermined number of closest data points are then added together and compared to a predetermined threshold. If the sum of the differences exceeds the predetermined threshold, the analyzed data point is discarded. Of course, the use of other clustering techniques to identify the most accurate data and to disregard probable inaccurate data is also within the scope of the present invention.

Once clustering has been performed, the inverse of the normalization is calculated, or the normalization is undone, to provide an accurate determination of pulmonary capillary blood flow or cardiac output. An example of the manner in which the inverse of the normalization may be calculated includes use of the following equation:

$$x=x\sigma_x+\bar{x}. \quad (21)$$

This inverse of the normalization is applied to all of the clustered x-axis (e.g., $CaCO_2$) values. A similar inverse normalization scheme is applied to all of the clustered y-axis data.

Clustering is one of many known techniques for determining outliers. Other known techniques for determining outliers may also be used in the method of the present invention.

Alternatively, or in addition to disregarding probable inaccurate data points, in order to enhance the accuracy of the data, clustering can be used to add synthetic data points. Synthetic data points may be added to increase the correlation coefficient of the best-fit line to the data points on which the best-fit line is based.

Figure 4A:
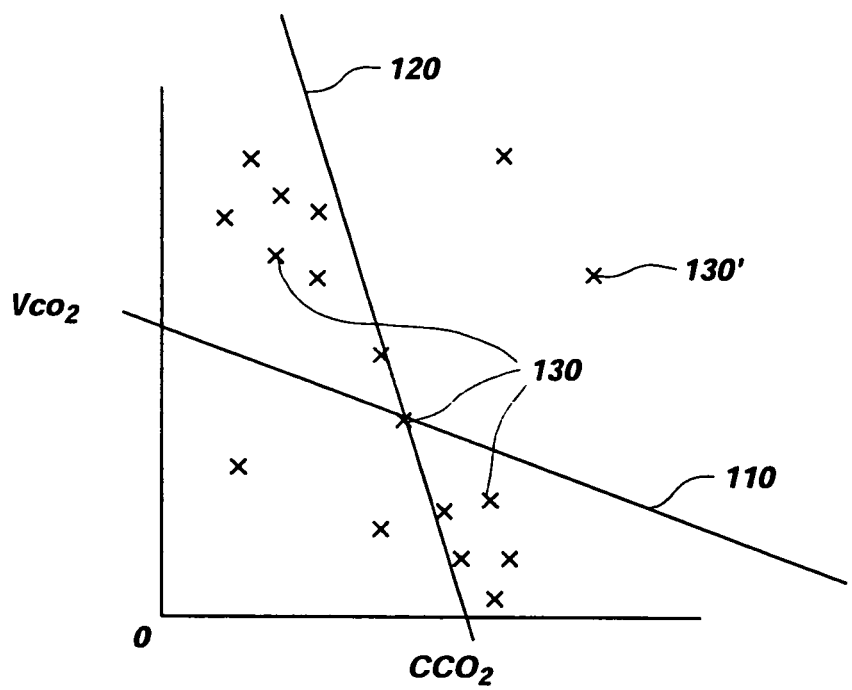
FIGS. 4A and 4B are two-dimensional plots illustrating an embodiment of a method for modifying data to obtain an accurate best-fit line therethrough in accordance with teachings of the present invention.
Figure 4B:
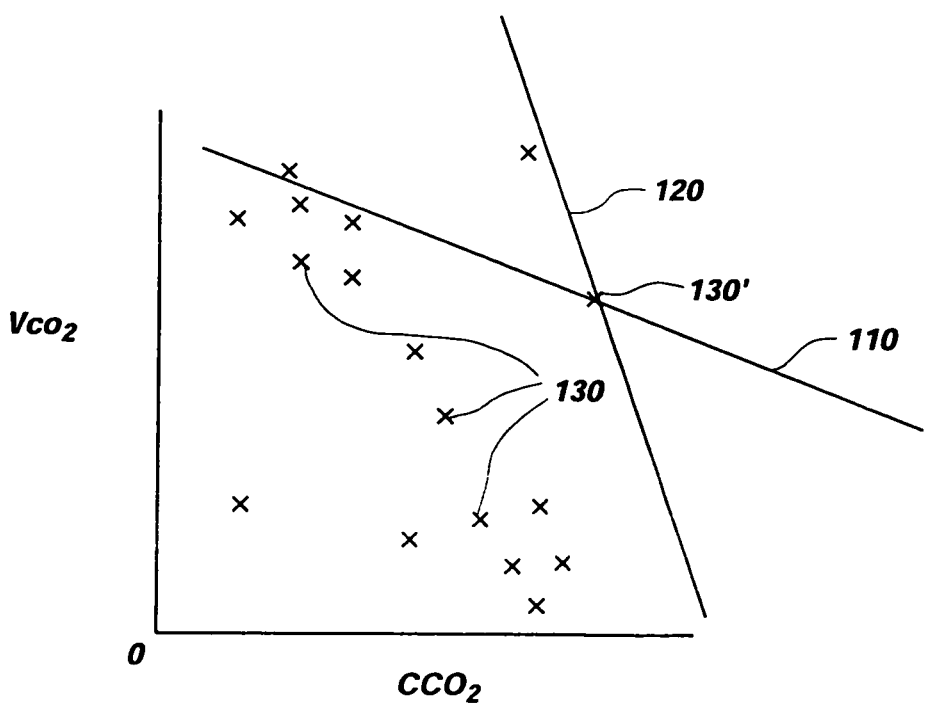

Another embodiment of the method for modifying data that incorporates teachings of the present invention is depicted in FIGS. 4A and 4B. As with the filtering and clustering embodiments described previously herein, the present embodiment includes selection of data points that are most likely to facilitate an accurate determination of the location and orientation of a best-fit line and, thus, of the pulmonary capillary blood flow or cardiac output of a patient. This embodiment of the method for modifying data includes iteratively examining data points and the distribution of the remaining data points relative to the two lines representing the range of possible PCBF measurements.

As shown in FIGS. 4A and 4B, a line or the equation for a line 110 representing a minimum expected pulmonary capillary blood flow (i.e., $-m_{line}=PCBF_{min}$) and a line or the equation for a line 120 representing a maximum expected pulmonary capillary blood flow (i.e., $-m_{line120}=PCBF_{max}$) are positioned to intersect at a data point 130. For example, when the x-ordinate is based on $CaCO_2$, line 110 may have a slope of −0.5, which represents a minimum expected pulmonary capillary blood flow of 0.5 L/min, and line 120 may have a slope of −20, which represents a maximum pulmonary capillary blood flow of 20 L/min. Of course, the use of other pulmonary capillary blood flow values for lines 110 and 120 is also within the scope of the present invention.

Next, the number of other data points 130 located between lines 110 and 120 is determined. If the number of data points 130 between lines 110 and 120 is equal to or exceeds a threshold number, the analyzed data point 130 is retained for a subsequent determination of the location and orientation of a best-fit line through the data. Otherwise, the analyzed data point 130 is discarded. The threshold number of data points that must be located between line 110 and line 120 for an analyzed data point to be retained may be a predetermined value or determined by other means. As an example, the threshold number may be set to the median number of data points that are located between line 110 and line 120 when each data point 130 of a set of data points 130 has been evaluated in accordance with the present embodiment of the method for modifying data. This process is repeated until each data point 130 in a set of data points 130 has been so evaluated. FIG. 4A depicts use of the present embodiment of the data modification method on a data point 130 that will be retained, while FIG. 4B illustrates use of the present embodiment of the data modification method on another data point 130' that will not be retained.

FIGS. 3C and 3D and FIGS. 5 and 6 illustrate the effect of modifying data in accordance with teachings of the present invention to increase the accuracy with which the location and orientation of a best-fit line through the data may be determined. FIG. 5 illustrates a typical $V_{CO_2}$ vs. $CaCO_2$ plot without such modification, where the plot appears as a loop. By way of contrast, FIG. 6 illustrates the closeness of the data when one or more of the embodiments of the method of the present invention are used to modify the data. FIGS. 3C and 3D illustrate plots of $V_{CO_2}$ and $PetCO_2$ data before and after modification in accordance with the present invention, respectively. The increased closeness of the data points makes it possible to determine the orientation and location of a best-fit line therethrough with increased accuracy.

Once all of the data points have been examined, the location and orientation for the best-fit line through the remaining, clustered data are determined. Again, linear regression is preferably used to determine the location and orientation of the best-fit line. The negative slope (i.e., −1×m) of the best-fit line provides a pulmonary capillary blood flow measurement, which may then be used to determine cardiac output. A correlation coefficient can then be calculated, as previously disclosed herein, to indicate the quality of the data used to determine pulmonary capillary blood flow or cardiac output. The correlation coefficient or a quality measure based thereon may then be communicated to the user (e.g., a doctor, nurse, or respiratory technician) or used to weight the resulting pulmonary capillary blood flow or cardiac output value in an output weighted average value.

One or a combination of the embodiments of the method for modifying data in accordance with the present invention may be performed on the measured or calculated data to increase the accuracy with which a best-fit line through the data or the pulmonary capillary blood flow or cardiac output of a patient can be determined.

As an example of the use of filtering and clustering together, the calculated $V_{CO_2}$ data are grouped together as the y-axis data of a two-dimensional line graph and the calculated $CaCO_2$ data points are grouped together as x-axis data points. The data points in at least one of the groups are filtered to determine a best-fit line for the data having an optimum correlation coefficient. The data are also clustered, either before or after filtering, to further improve the correlation coefficient of the best-fit line to the calculated $V_{CO_2}$ and $CaCO_2$ data. The remaining data is then used to determine (e.g., by linear regression) a best-fit line therefor, as well as a correlation coefficient for the best-fit line. The slope of the best-fit line is then calculated and used to determine pulmonary capillary blood flow or cardiac output. The correlation coefficient may also be used to indicate the reliability of the pulmonary capillary blood flow or cardiac output determination or to impart a specific weight to the pulmonary capillary blood flow or cardiac output determination in a weighted average thereof.

Once the location and orientation of an accurate best-fit line for the data has been determined, as disclosed previously herein, the pulmonary capillary blood flow of the patient can be calculated as the negative of the slope of the best-fit line. In addition, cardiac output can then also be determined by adding the pulmonary capillary blood flow of the patient to the intrapulmonary shunt flow of the patient, which can be determined by known processes.

In addition, the best-fit line can be used to estimate mixed venous carbon dioxide content of the patient. Conventionally, total rebreathing techniques have been required to substantially noninvasively measure mixed venous carbon dioxide content. When carbon dioxide elimination eventually ceases during total rebreathing, the partial pressure of carbon dioxide measured at the mouth of a patient may represent the mixed venous carbon dioxide content of the patient. When partial rebreathing techniques are used, the carbon dioxide elimination of the patient is reduced to levels lower than baseline, but is not reduced to zero. By employing teachings of the present invention to determine the best-fit line through data obtained by use of partial rebreathing techniques, the best-fit line can be extended to a point where carbon dioxide elimination would be equal to zero or effectively zero and thereby to determine the carbon dioxide content, or mixed venous carbon dioxide content, of the patient's blood at that point. Equation (11), which is a derivative of the equation for the best-fit line, can be rearranged in terms of carbon dioxide elimination as follows:

$$V_{CO_2} = m \times CaCO_2 + b, \quad (22)$$

When carbon dioxide elimination ceases, $V_{CO_2}$ is equal to zero and equation (22) becomes:

$$0 = m \times CvCO_2 + b, \quad (23)$$

where $CvCO_2$ is the mixed venous carbon dioxide content, which can be rearranged as follows:

$$CvCO_2 = -b/m. \quad (24)$$

Accordingly, the present invention also includes a method for substantially noninvasively determining mixed venous carbon dioxide content when partial rebreathing techniques are employed.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A system for substantially non-invasively determining at least one of a pulmonary capillary blood flow and a cardiac output of a subject, comprising:
    a breathing conduit;
    a flow sensor in communication with the breathing conduit;
    a gas sensor in communication with the breathing conduit; and
    at least one processing element for receiving signals including measured data points from the flow sensor and the gas sensor, the at least one processing element being configured to:
        retain data points of the measured data points when a number of the data points within a location is equal or greater than a specified threshold; and
        discard data points of the measured data points when the number of the data points within the location is less than the specified threshold.

2. The system of claim 1, wherein the gas sensor comprises a carbon dioxide sensor.

3. The system of claim 1, wherein the at least one processing element is programmed to calculate an estimate of carbon dioxide elimination and an estimate of carbon dioxide content of the subject's blood.

4. The system of claim 1, wherein the at least one processing element is programmed to filter the data points with an algorithmic filter.

5. The system of claim 1, wherein the at least one processing element is programmed to identify a substantially linear relationship between the data points.

6. The system of claim 5, wherein the at least one processing element is programmed to calculate a correlation coefficient between the data points and a best fit line of the substantially linear relationship.

7. The system of claim 6, wherein the at least one processing element is also programmed to increase the correlation coefficient.

8. The system of claim 1, further comprising:
    a ventilation control element configured to facilitate a change in effective ventilation by the subject.

9. The system of claim 1, further comprising:
    an output element for outputting at least one of a pulmonary capillary blood flow and a cardiac output.

10. The system of claim 1, wherein the specified threshold comprises a selected number of data points of the measured data points that are within a predetermined distance to a data point being analyzed by the at least one processing element for determining whether to retain or discard the data point being analyzed.

11. The system of claim 1, wherein the at least one processing element is configured to discard the data points by performing the acts of:
- clustering the measured data points in groups by searching for a predetermined number of closest data points to each of the data points in a group;
- adding differences between a data point being analyzed and each of the predetermined number of closest data points to obtain a sum of the differences;
- comparing the sum of the differences to a predetermined threshold; and
- discarding the data point when the sum of the differences exceeds the predetermined threshold.

12. A system for substantially non-invasively determining at least a pulmonary capillary blood flow of a subject, comprising:
- a flow sensor in communication with a breathing circuit;
- a gas sensor in communication with the breathing circuit;
- means for causing a change in effective ventilation of the subject; and
- at least one processing element for receiving signals including measured data points from the flow sensor and the gas sensor, the at least one processing element being configured to:
- retain data points of the measured data points when a number of the data points within a location is equal or greater than a specified threshold; and
- discard data points of the measured data points when the number of the data points within the location is less than the specified threshold.

13. The system of claim 12, further comprising:
- means for outputting at least one of a pulmonary capillary blood flow and a cardiac output of the patient.

14. The system of claim 12, wherein the specified threshold comprises a selected number of data points of the measured data points that are within a predetermined distance to a data point being analyzed by the at least one processing element for determining whether to retain or discard the data point being analyzed.

15. The system of claim 12, wherein the at least one processing element is further configured to discard the data points by performing the acts of:
- clustering the measured data points in groups by searching for a predetermined number of closest data points to each of the data points in a group;
- adding differences between a data point being analyzed and each of the predetermined number of closest data points to obtain a sum of the differences;
- comparing the sum of the differences to a predetermined threshold; and
- discarding the data point when the sum of the differences exceeds the predetermined threshold.

* * * * *